(12) United States Patent
Vargo et al.

(10) Patent No.: US 10,456,068 B2
(45) Date of Patent: Oct. 29, 2019

(54) DEVICE FOR OBTAINING SMALL, PRECISE VOLUMES OF FLUID FROM ANIMALS

(71) Applicants: John V. Vargo, Turbotville, PA (US); Louis M. Bassler, Montoursville, PA (US); Troy L. Ott, Spring Mills, PA (US); Robert W. VanDine, Montoursville, PA (US)

(72) Inventors: John V. Vargo, Turbotville, PA (US); Louis M. Bassler, Montoursville, PA (US); Troy L. Ott, Spring Mills, PA (US); Robert W. VanDine, Montoursville, PA (US)

(73) Assignees: Med-Ag Industries, Inc., Montoursville, PA (US); The Penn State Research Foundation, University Park, PA (US)

(*) Notice: Subject to any disclaimer, the term of this patent is extended or adjusted under 35 U.S.C. 154(b) by 189 days.

(21) Appl. No.: 15/336,917

(22) Filed: Oct. 28, 2016

(65) Prior Publication Data
US 2017/0119294 A1     May 4, 2017

Related U.S. Application Data

(60) Provisional application No. 62/248,370, filed on Oct. 30, 2015.

(51) Int. Cl.
    *A61B 5/00*     (2006.01)
    *A61B 5/15*     (2006.01)
    (Continued)

(52) U.S. Cl.
CPC .... *A61B 5/150343* (2013.01); *A61B 5/15003* (2013.01); *A61B 5/150022* (2013.01); *A61B 5/15186* (2013.01); *A61B 5/153* (2013.01); *A61B 5/155* (2013.01); *A61B 5/15105* (2013.01); *A61B 5/150305* (2013.01); *A61B 5/150358* (2013.01); *A61B 5/150389* (2013.01); *A61B 5/150412* (2013.01);
(Continued)

(58) Field of Classification Search
CPC ........ A61B 5/150022; A61B 5/150267; A61B 5/150343
See application file for complete search history.

(56) References Cited

U.S. PATENT DOCUMENTS 281,543 A     7/1883    Mayo
690,236 A    12/1901    Colwell
(Continued)

*Primary Examiner* — Max F Hindenburg
(74) *Attorney, Agent, or Firm* — Wendy W Koba

(57) ABSTRACT

A "one-step", single-handed device for obtaining small, precise volumes of fluid from animals is able to quickly and easily draw a fluid sample. The device comprises an extraction component and a collection component that are coupled together and disposed along a grip handle. The user manipulates the device so as to initiate the extraction of the fluid, and then collect the fluid in a component that can quickly and easily be removed from the grip handle—allowing the handle to be re-loaded and used again and again. The extraction component may comprise a hypodermic needle and the collection component may comprise a pre-calibrated pipette, where the pipette is positioned directly behind the needle and will thus draw the extracted fluid into a pre-sized chamber within the pipette.

12 Claims, 9 Drawing Sheets

(51) Int. Cl.
  *A61B 5/151* (2006.01)
  *A61B 5/153* (2006.01)
  *A61B 5/155* (2006.01)
  *B01L 3/02* (2006.01)

(52) U.S. Cl.
  CPC ... *A61B 5/150458* (2013.01); *A61B 5/150503* (2013.01); *A61B 5/150587* (2013.01); *A61B 5/150717* (2013.01); *A61B 5/150732* (2013.01); *A61B 2503/40* (2013.01); *B01L 3/021* (2013.01)

(56) References Cited

U.S. PATENT DOCUMENTS

| | | | |
|---|---|---|---|
| 1,140,186 A | | 5/1915 | Quick |
| 3,785,366 A | * | 1/1974 | Davis ............... A61B 10/02 600/562 |
| 4,493,700 A | | 1/1985 | Cassou et al. |
| 4,654,025 A | | 3/1987 | Cassou et al. |
| 5,830,410 A | * | 11/1998 | Thieme ............. A61B 10/0051 422/419 |
| 7,056,279 B2 | | 6/2006 | Verberckmoes et al. |
| 8,652,802 B2 | | 2/2014 | Rutty et al. |
| 8,715,593 B2 | * | 5/2014 | Brewer ............... B01L 3/0275 422/501 |
| 9,072,472 B2 | | 7/2015 | Potter et al. |
| 9,408,568 B2 | * | 8/2016 | Fletcher ............. A61B 5/1411 |
| 10,080,516 B2 | * | 9/2018 | Ellis ................. A61M 1/36 |
| 10,092,230 B2 | * | 10/2018 | Schraga ........... A61B 5/15003 |
| 2011/0282135 A1 | | 11/2011 | Waybright |
| 2015/0320347 A1 | | 11/2015 | Piacentini et al. |

* cited by examiner

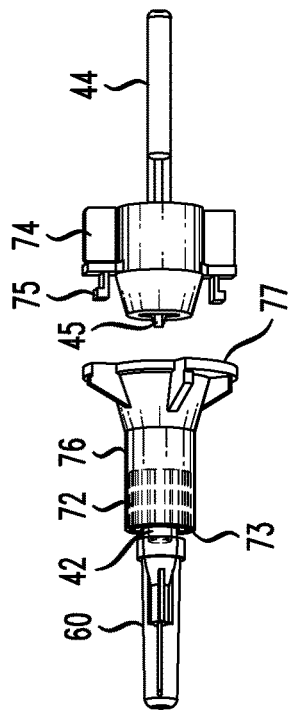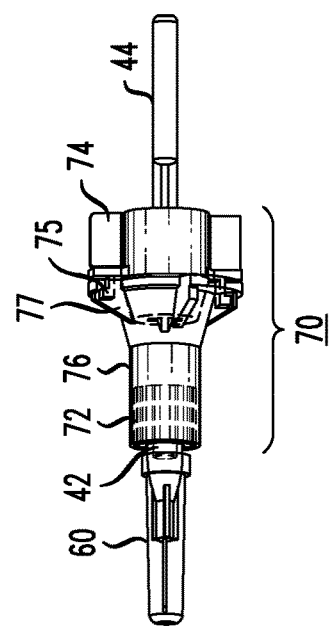
FIG. 9
FIG. 10

DEVICE FOR OBTAINING SMALL, PRECISE VOLUMES OF FLUID FROM ANIMALS

CROSS-REFERENCE TO RELATED APPLICATIONS

This application claims the benefit of U.S. Provisional Application Ser. No. 62/248,370, filed Oct. 30, 2015 and herein incorporated by reference.

This invention was made with government support under Hatch Act Project No. PEN04511, awarded by the United States Department of Agriculture/NIFA. The Government has certain rights in the invention.

TECHNICAL FIELD

The present invention relates to a device for obtaining small, precise volumes of fluid from animals and, more particularly, to a collection device that is able to pierce the hide of an animal with minimal discomfort to collect this precise volume of a fluid.

BACKGROUND OF THE INVENTION

There is an increasing need to perform various types of diagnostic tests on animals of all types. For example, animal species such as bovinae, equidae, caprinae, suidae and a variety of poultry and other ayes (whether domestic or wild) are reservoirs of human pathogens. Organizations and veterinary professionals that are tasked with monitoring the health of the animals and the safety of the human food supply need timely and accurate information about the health status of animals. Furthermore, other sensitive diagnostic tests are available or in development for assessing metabolic and reproductive status of animals. These tests require obtaining precise and accurate small volumes of fluid or tissue from animals.

In the case of farm animals, such as cow (for example), the ability to obtain precise (especially small) volumes (e.g., less than 1000 µL and especially less than 100 µL) of fluid or tissue samples (for example, a blood sample) in one step without the need for additional pipetting steps is currently not possible. Conventional techniques for obtaining samples often require more than one person, as well as sample movement between different locations using a combination of sampling devices and pipetting devices. In some cases, this expected delay between obtaining a large, imprecise, volume of blood and subsequent sub-sampling requires that an anticoagulant be added to the sample to prevent clotting until the sub-sampling is possible. Anticoagulants can interfere with some diagnostic assays. The sampling approach used in domestic and wild animals may also create challenges for the clinician, including the possibility of being dangerous to the well-being of the clinician. There are various types of needles, lancets or other piercing devices that may be handled as individual components or attached to a syringe and inserted into a vessel proximal to the skin of the animal. In some instances a needle is inserted and then a separate tube, or similar collection device is attached to the needle and used to collect the sample in volumes ranging from 3 to several 100 milliliters, often with an anticoagulant. This sample is then transported to a nearby area (e.g., a laboratory) where a precise volume of the sample is removed from the larger sample for application in a variety of assay platforms.

With the tremendous advances in the sensitivity of a variety of diagnostic tests there is a real need for a one step process that allows animal health care professionals to obtain precise and accurate small volumes of fluid or tissue in one step (e.g., 10-100 µL), without the need for additional pipette sub-sampling and in some instances without the use of anticoagulant.

SUMMARY OF THE INVENTION

The needs remaining in the prior art are addressed by the present invention, which relates to a device for obtaining small volumes of fluid from animals and, more particularly, to a collection device that is able to pierce the hide of an animal and collect a precise volume of a fluid.

In accordance with one exemplary embodiment of the present invention, a "one-step", single-handed device is proposed that is able to quickly and easily draw a fluid sample from an animal. The device comprises an extraction component and a collection component that are coupled together and disposed along with a grip handle. The user manipulates the device so as to initiate the extraction of the fluid, and then collect the fluid in a component that can quickly and easily be removed from the grip handle—allowing the handle to be re-loaded and used again and again.

In accordance with another embodiment of the present invention, the extraction component comprises a hypodermic needle and the collection component comprises a pre-calibrated pipette, where the pipette is positioned directly behind the needle and will thus draw the extracted fluid into a pre-sized chamber within the pipette.

One exemplary configuration of the pipette embodiment utilizes a collection device comprising a plurality of pipettes, where a single needle stick allows for multiple pipettes to be filled at the same time.

An alternative embodiment of the present invention utilizes a lancet as the extraction component and an absorbent swab as the collection component, the components are disposed on opposite ends of a grip handle. In this embodiment, once the animal's hide has been pierced with the lancet, the user turns the device around and collects the fluid onto the absorbent material. Thereafter, the swab is removed from the grip handle (perhaps a snap release), and placed into a test vial.

Other and further embodiments of the present invention will become apparent during the course of the following discussion and by reference to the accompanying drawings.

BRIEF DESCRIPTION OF THE DRAWINGS

Referring now to the drawings, where like numerals represent like numbers in several views:

FIG. 9 illustrates the embodiment of FIG. 7 with the pipette also positioned within the quick-release mechanism;

FIG. 10 shows the embodiment of FIG. 7 in its fully assembled, ready-to-use form;

DETAILED DESCRIPTION

As will be discussed in detail below, the present invention relates to a fluid collection device that functions to both pierce the hide of the animal and precisely and accurately collect a small volume of the required fluid sample in one step. As will be discussed below, the collection device of the present invention includes a fluid extraction component to pierce the skin of the animal and initiate the fluid flow (e.g., a lancet or needle) disposed at one end of the device and fluid collection component (e.g., an absorbent swab or pipette) disposed at the opposing end.

Figure 1:
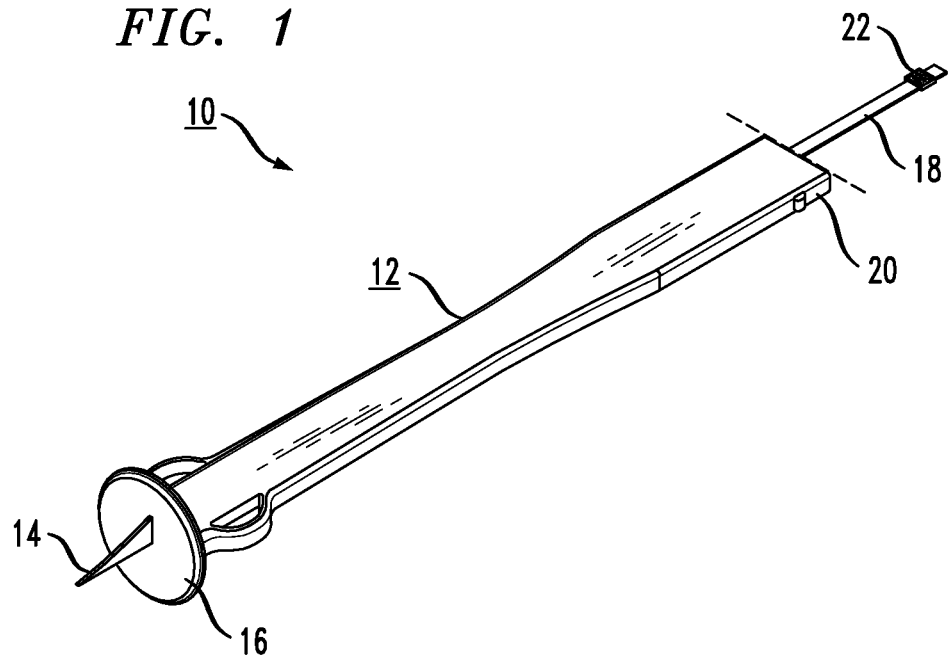
FIG. 1 illustrates an exemplary fluid collection device including a lancet as an extraction component and an absorbent swab as a collection component formed in accordance with the present invention.
Figure 2:
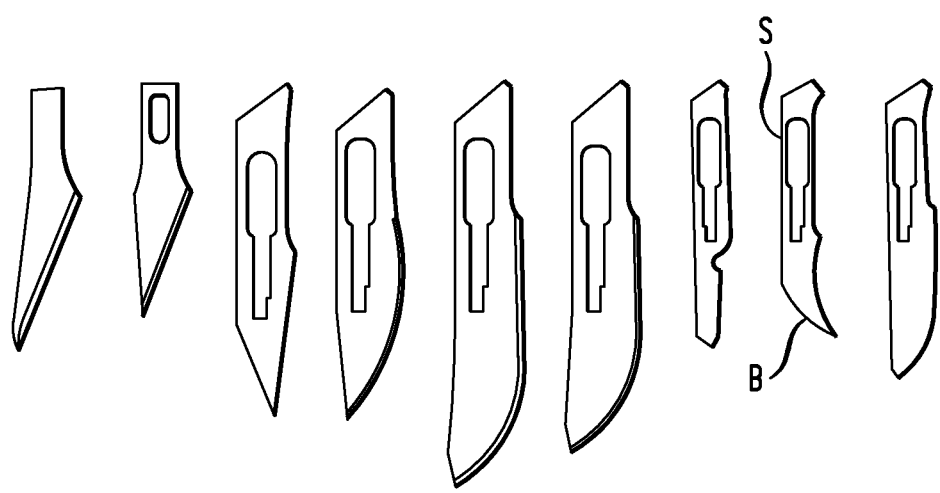
FIG. 2 depicts a plurality of different lancet configurations for use in the collection device of the present invention.

FIG. 1 illustrates a first embodiment of an exemplary collection device 10 formed in accordance with the present invention. As shown, device 10 comprises a grip handle 12, with a fluid extraction component in the form of a lancet 14 disposed within a first end portion 16 of grip handle 12. For the sake of completeness, various types of typical lancets are shown in FIG. 2. The lancets may be of various lengths (including both the length of the sheath S and blade B). As mentioned above, it is an ordinary practice for an individual to utilize the lancet "as is" and attempt to pierce the animal hide and then draw a sample of fluid.

Returning to the description of FIG. 1, first end portion 16 of grip handle 12 is shown as being oversized in surface area when compared to the remainder of handle 12. The intent of this enlarged end portion 16 is to allow for end portion 16 to function as a "landing surface", so that as an individual uses the collection device, the motion of the handle towards the animal will introduce lancet 14 into the hide, with end portion 16 providing stability to this piercing action while restricting the depth of the piercing to that optimal for sample collection. In the particular embodiment of FIG. 1, end portion 16 exhibits a circular surface area, which is considered preferable for certain purposes. However, other geometries of end portion 16 (including rectangular or square) are possible.

In the particular embodiment shown in FIG. 1, collection device 10 further comprises a collection component in the form of a break-away test swab 18 attached to the opposing end termination 20 of grip handle 12. As shown, an absorbent material 22 (such as a suitable type of flocking) is included at the tip of test swab 18.

Thus, to use collection device 10, an individual would grip handle 12 in a manner such that lancet 14 faces the animal. The individual then uses device 10 to pierce the hide with lancet 14. Upon withdrawing the lancet, the individual merely rotates collection device 10 in the opposite direction, with test swab 18 facing the animal. The individual then uses absorbent material 22 to collect the necessary (in many situations, precise) fluid volume from the animal.

As described, the process of using the inventive collection device allows for a "single-handed" one step piercing and collection of a precise and accurate volume of fluid. Once the fluid has been collected, break-away test swab 18 may be inserted into an associated vial or other test-related instrument (not shown), where it is easily snapped off of grip handle 12 so that only swab 18 enters the testing instrument.

Figure 3:
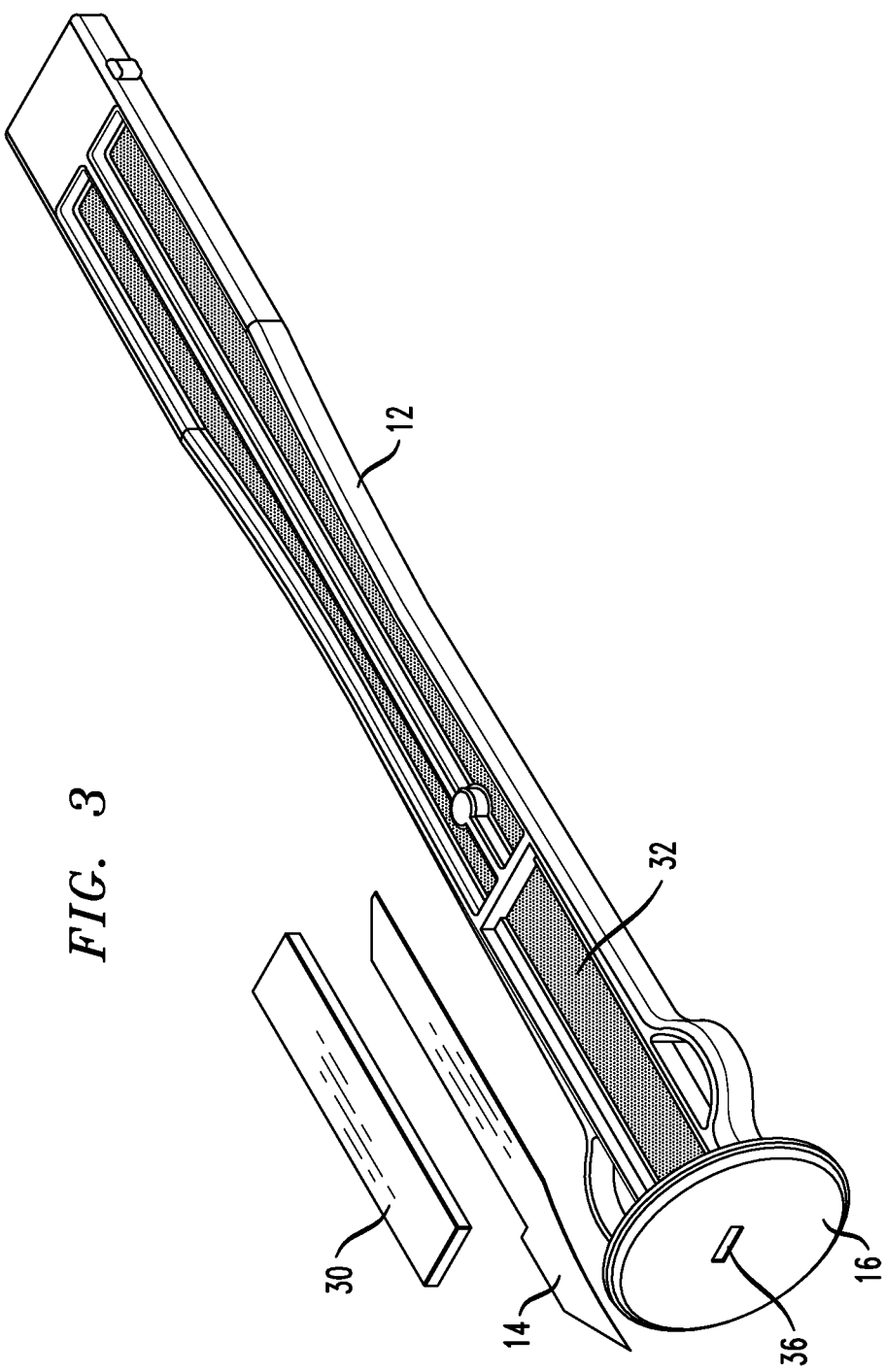
FIG. 3 is an exploded view of the collection device of FIG. 1.

There are various materials that may be used to form grip handle 12 including, but not limited to, plastics, pressed paper, composites, metals, and the like. In some embodiments the lancet may be permanently embedded within grip handle 12. In other embodiments, grip handle 12 may be formed to include a removable cover such that the individual may select a particular lancet size that is best-suited for a particular procedure and insert the lancet in the grip handle prior to use. FIG. 3 illustrates this particular configuration of the embodiment of FIG. 1 in an exploded view. As shown, a press-fit cover 30 is included in an end section of grip handle 12 and is removable by the user. Once removed, a recessed area 32 within grip handle 12 is exposed. Recessed area 32 is sized to support a selected lancet 14 (or other suitable fluid extraction component), where the individual lays lancet 14 in recessed area 32 in a manner such that the sheath S is supported within recessed area 32 and the blade B passes through an aperture 36 in end portion 16 so that it extends beyond the termination of grip handle 12 (as shown in FIG. 1).

Figure 4:
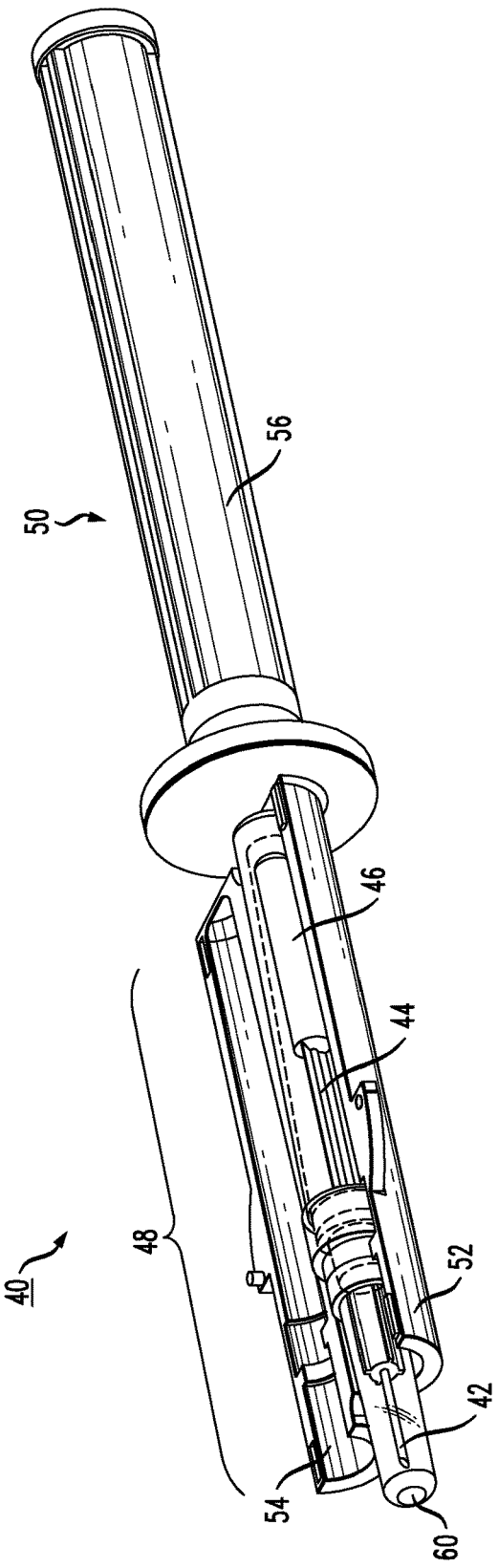
FIG. 4 illustrates another embodiment of an exemplary fluid collection device including a hypodermic needle extraction component and a pipette collection component formed in accordance with the present invention.
Figure 5:
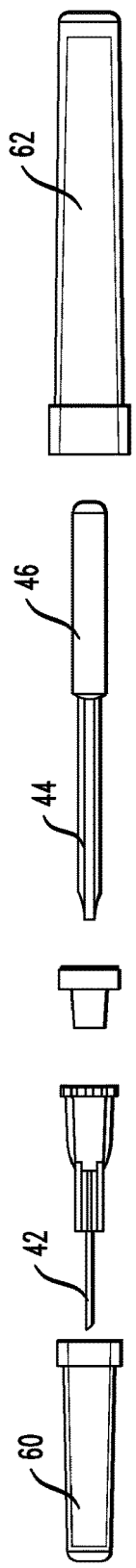
FIG. 5 is an exploded view of the fluid collection device of FIG. 4.

FIG. 4 illustrates an alternative embodiment of the present invention. In this configuration, a fluid collection device 40 is formed to include a fluid extraction component in the form of a hypodermic needle 42 that is used to pierce the animal's hide and access a fluid-filled compartment (e.g., a blood vessel). FIG. 5 is an exploded view of the individual elements forming fluid collection device 40. Referring to both FIGS. 4 and 5, the escaping fluid/tissue travels through needle 42 via capillary action and into a fluid collection component in the form of a pre-calibrated pipette 44 attached to needle 42. In particular, pre-calibrated pipette 44 is configured to include a bulbous portion 46 that is sized to collect a predetermined volume of fluid and facilitate its expulsion from pipette 44. There are a variety of applications where the ability to collect a precise volume is important. For example, a critical aspect of a lateral flow assay which uses a direct sample is the need to collect "precise" volume to indicate an accurate cutoff value for positive versus negative determination. Not all protein assays (i.e., ELISA) need a precise volume. However, there are a significant number of lateral flow tests that require the collection of precise volumes of fluid (in the range of, for example, +/−10%). The configurations of the present invention as described above and below are able to draw this precise volume.

Once the procedure is completed, the user extracts needle 42 from the animal and removes pipette 44 from the apparatus. The user is then able to squeeze the bulbous portion 46 of pipette 44 and transfer a precise volume of fluid into a test vial (not shown). In accordance with the present invention, both the used needle 42 and used pipette 44 are thereafter disposed of (following proper protocols for disposal of such materials). Grip handle 50 may then be re-loaded with a clean needle and pipette to prepare for the next procedure. As shown in FIG. 4, all three of these elements are positioned within a first section 48 of an instrument grip handle 50, which is preferably configured to easily fit into the hand of a clinician, phlebotomist or sampling technician.

Figure 6:
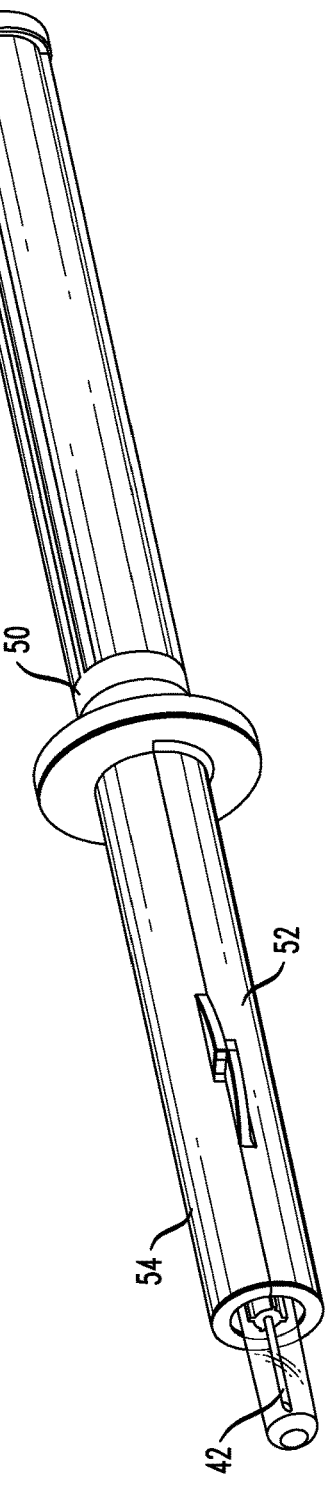
FIG. 6 illustrates the device of FIG. 4 in a fully-assembled, ready to use form.

In the view of FIG. 4, first section 48 of instrument grip handle 50 is shown as comprising a clam-shell type of configuration, including a lower half 52 (shown as support for the above-described fluid collection elements), and an upper half 54 that will fit over lower half 52 and fixedly hold the collection elements in place. FIG. 6 is a view showing upper half 54 in place over lower half 52, thus enclosing pipette 44 and preventing movement between needle 42 and pipette 44. Obviously the cover 60 over needle 42 is removed proper to use.

As with the embodiment of FIG. 1, collection device 40 as shown in FIGS. 4-6 is capable of one-handed use and can easily obtain a precise and accurate fluid sample volume (especially very small volumes) from an animal. In use, an individual grips a rear section 56 of grip handle 50 and directs needle 42 (or other suitable fluid extraction component) through the animal's hide and into a blood vessel. It is to be noted that in these various views needle 42 is covered by a protective end cap 60 (and pipette 44 may be disposed within a removable cover 62, as also shown). Obviously, end cap 60 is removed prior to use. Preferably, end cap 60 is formed of a material that is not harmful to animals if ingested, in case the cap becomes lost after the sample is collected.

Figure 7:
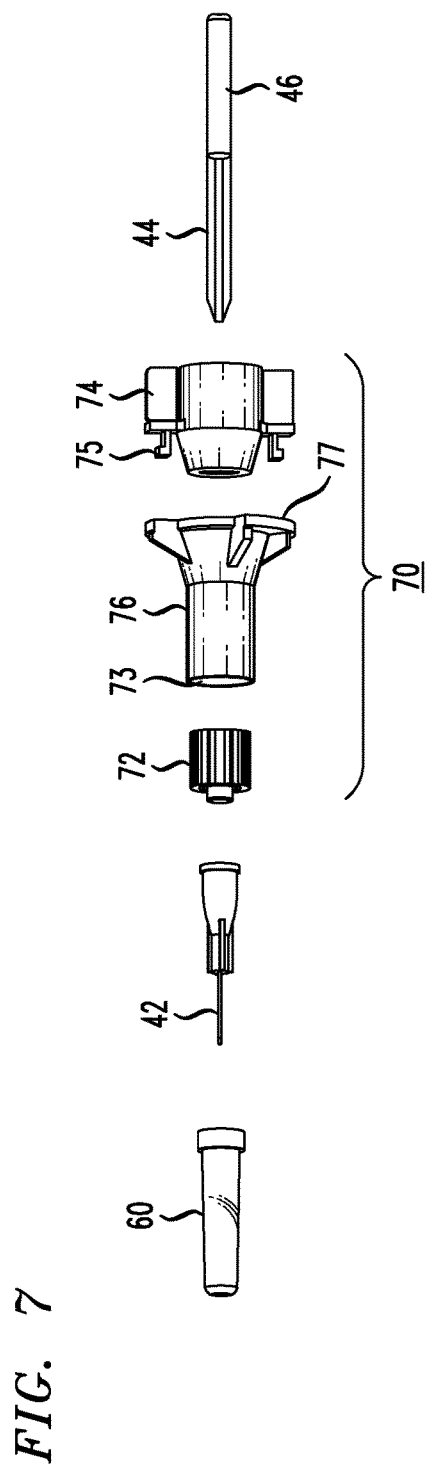
FIG. 7 is an exploded view of an alternative configuration of the embodiment of FIG. 4, including a quick-release mechanism to remove a filled pipette from the device.

FIG. 7 is an exploded view of an alternative configuration for providing attachment between the extraction and collection components when designing collection device 40 (as shown in FIG. 4). The embodiment of FIG. 7 provides a particular quick-release assembly 70 between needle 42 and pipette 44 that is easy to handle and efficiently remove pipette 44 from the device once the fluid collection process is completed. Various types of quick-release assemblies are available and are known to those skilled in the art to which the invention pertains.

Similar to the arrangement of FIGS. 4-6, the configuration shown in FIG. 7 uses needle 42 as the fluid extraction component and pipette 44 as the fluid collection component. In contrast to the configuration of FIG. 4, the arrangement as shown in FIG. 7 includes a quick-release assembly 70 to provide releasable attachment between needle 42 and pipette 44.

Referring to FIG. 7, needle 42 is positioned to engage a first end component 72 of quick-release assembly 70. Pipette 44 is disposed to fit within a second, rear end component 74 of quick-release assembly 70. An intermediate component 76 of quick-release assembly 70 is used to support both first end component 72 and second end component 74 in the manner shown such that the open end of pipette 44 is aligned with needle 42, allowing the fluid to enter pipette 44.

In particular, first end component 72 is sized to fit within a first end opening 73 of intermediate component 76. In this embodiment, second end component 74 is shown as including locking pins 75 that engage with lock locations 77 formed within intermediate component 76. In this manner, the combination of pipette 44 and rear end component 74 may easily be "unlocked" and removed from the remainder of the device once the sample has been collected.

With this arrangement, the user is able to disengage the needle from the quick-release handle by holding only the handle itself (that is, without needing to touch the pipette). Once removed from the sampling handle component, the user is able to transfer the fluid from the pipette to a test tube/test surface in a conventional manner.

Figure 8:
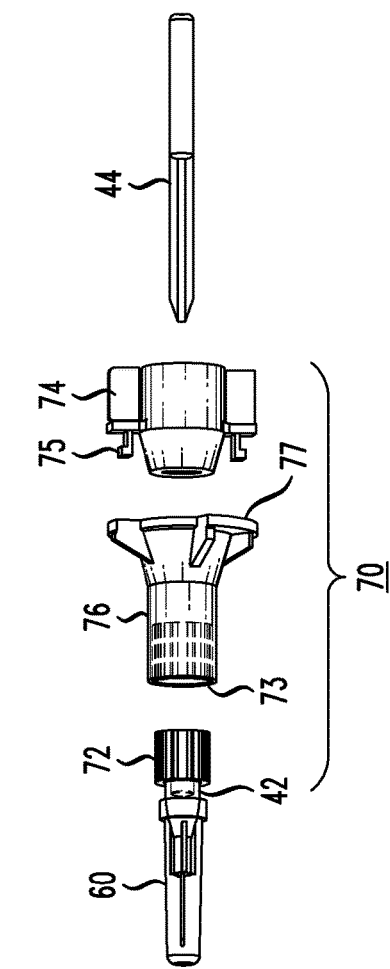
FIG. 8 is a view of the arrangement of FIG. 7, showing the needle positioned with the quick-release mechanism.

FIG. 8 is a view of the arrangement of FIG. 7, in this case illustrating needle 42 as positioned within first end component 72 of quick-release assembly 70. FIG. 9 shows first end component 72 positioned within first end opening 73 of intermediate component 76, and pipette 44 inserted in place within second, opposing, end component 74. A tip 45 of pipette 44 is visible in this view as extending beyond second end component 74.

Figure 11:
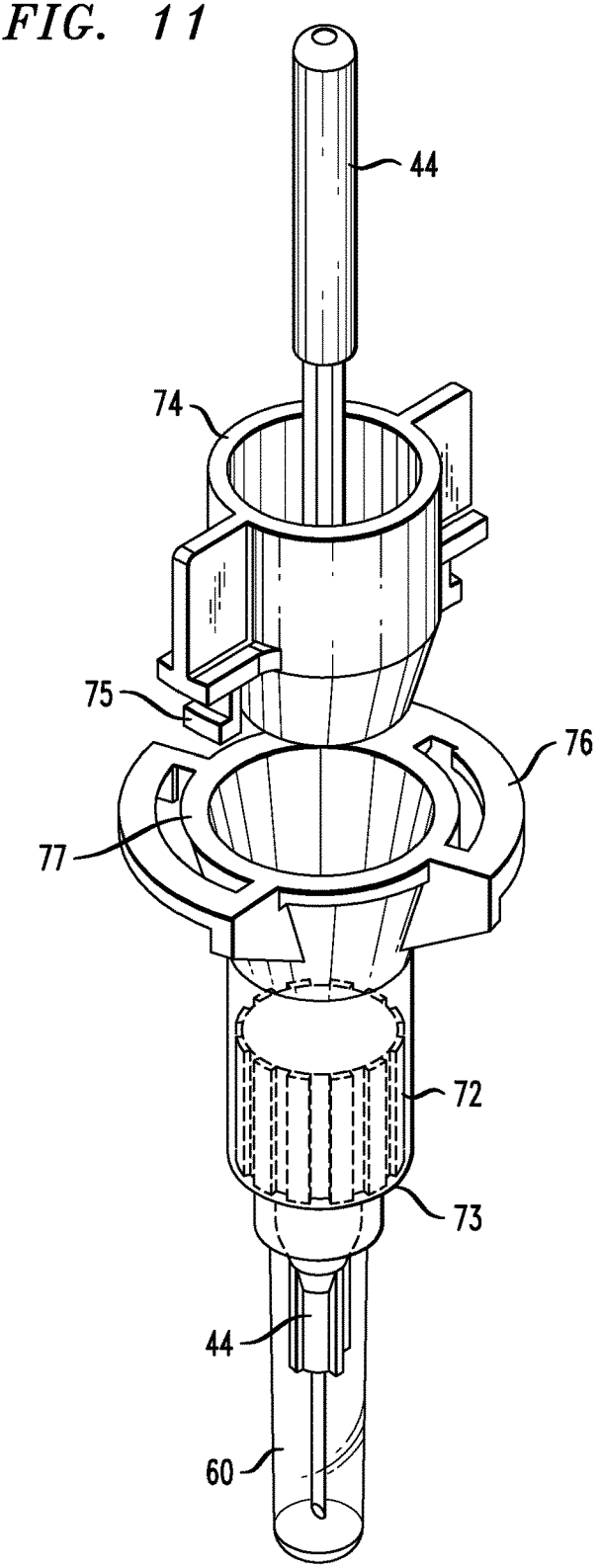
FIG. 11 is an isometric view of the assembled collection device of FIG. 10.

FIG. 10 illustrates this embodiment of the present invention in its completely assembled form, with locking pins 75 of second end component 74 engaging with intermediate component 76. FIG. 11 is an isometric view of this embodiment from another perspective. Here, the insertion of pipette 44 into second end component 44 is clearly shown. Also evident in this view is the positioning and interworking of locking pins 75 with lock locations 77.

Figure 12:
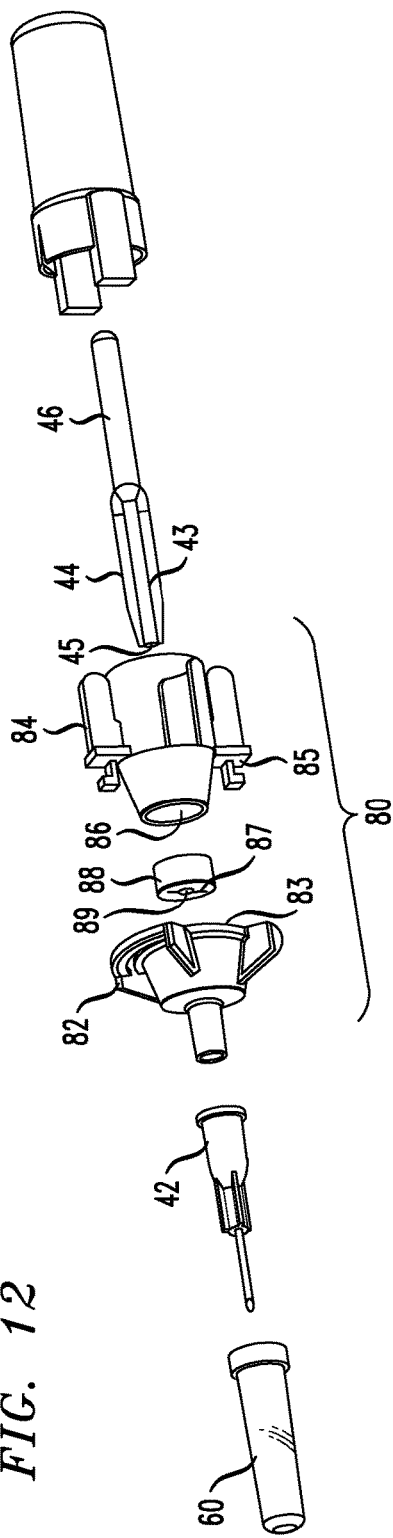
FIG. 12 illustrates yet another configuration with an alternative quick-release mechanism.

FIG. 12 illustrates an alternative type of locking component that may be utilized to releasably attach pipette 44 to needle 42. In this example, a releasable attachment assembly 80 is used to secure both needle 42 and pipette 44 in place, while providing a simplified process for removing pipette 44 at the end of the procedure. In particular, releasable attachment assembly 80 includes a first end component 82 for supporting needle 42 in a press-fit arrangement, where needle 42 may be easily removed from first end component 82 and disposed of in accordance with standard medical practices at the end of the procedure.

Releasable attachment assembly 80 further comprises a second end component 84, which includes a central bore 86. Pipette 44 is inserted in place within attachment assembly 80 via bore 86 in the manner shown in FIG. 12. A sealing disk 88 is disposed between end components 82 and 84. Sealing disk 88 includes a central bore 89 sized to accept the open, tip end 45 of pipette 44. A pair of longitudinal slots 87 is formed in sealing disk 88 for aligning with and engaging fins 43 of pipette 44. The addition of sealing disk 88 maintains the integrity of the path for fluid flow and minimizes the possibility of leakage.

Releasable attachment between pipette 44 and needle 42 is provided in this configuration by the use of locking pins 85 (on second end component 84) engaging and operating with locking surfaces 83 on first end component 82.

Figure 13:
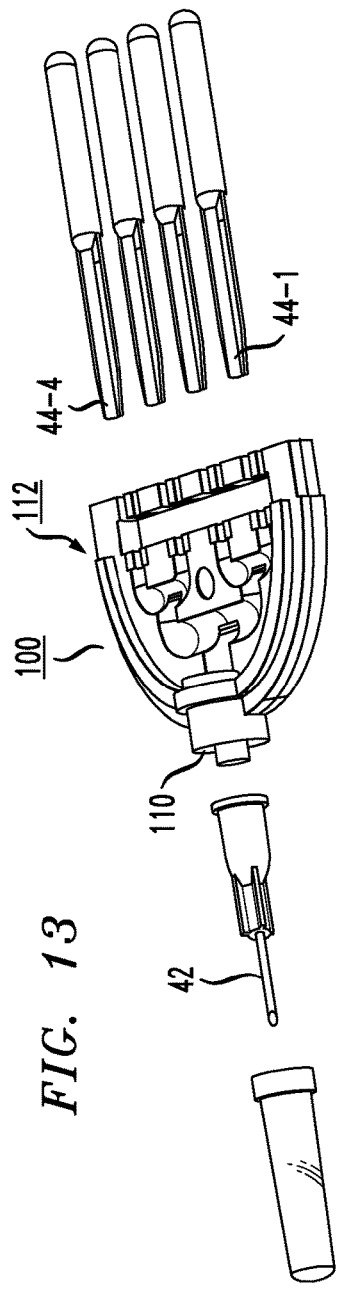
FIG. 13 shows another embodiment of a collection device formed in accordance with the present invention, where the collection component is configured to support multiple pipettes.
Figure 14:
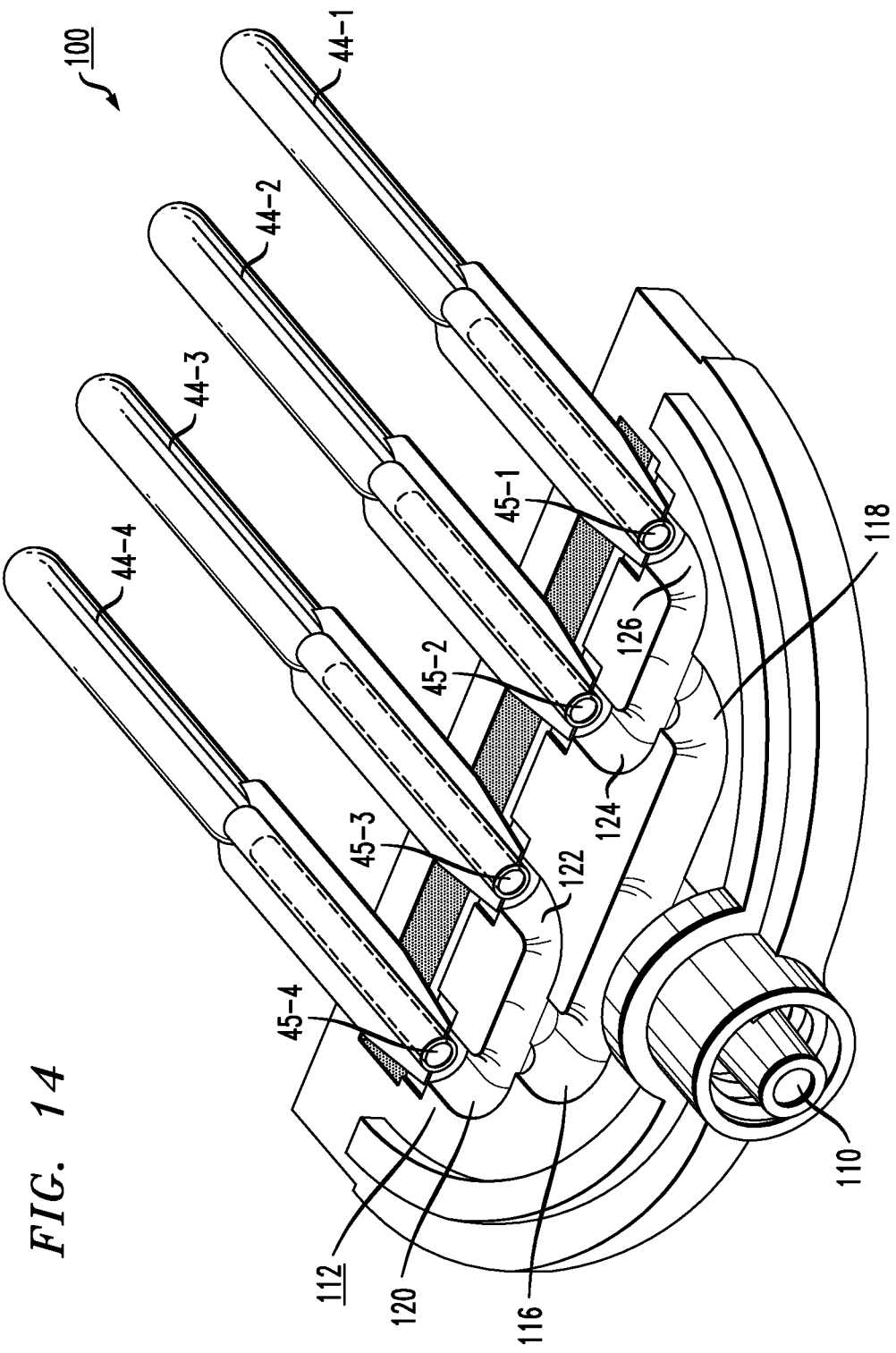
FIG. 14 is a close-up, isometric view of the collection component of FIG. 13, showing a tree-and-branch configuration for dispersing the fluid into the multiple pipettes.

It is also contemplated that the collection device of the present invention may also be used in situations where it is necessary to draw multiple samples from an animal. Accordingly, an exemplary embodiment of the present invention as shown in FIG. 13 includes a collection component 100 that is able to support (and fill) multiple pipettes during a single procedure. FIG. 14 is an enlarged view of collection component 100.

Referencing both FIGS. 13 and 14, collection component 100 is shown as including first end element 110 that engages with needle 42 in a manner similar to the various embodiments described above. In this case, however, the fluid exiting (via capillary action) from needle 42 enters a channel system 112 formed in collection component 100. As best seen in FIG. 14, channel system 112 includes a first divided path 114, which is configured such that the fluid being collected evenly passes along both branches of divided path 114, shown as branches 116 and 118 in FIG. 14. Another level of branching is included in this particular embodiment, where as shown branch 116 is again split into two separate branches, shown as channels 120 and 122 in FIG. 14. Similarly, branch 188 splits into two branches, shown as channels 124 and 126.

As further shown, a first pipette 44-1 is disposed along channel 126, where tip 45-1 of pipette 44-1 is positioned to collect the fluid passing along channel 126. A second pipette 44-2 is similarly disposed along channel 124. Thus, pipettes 44-1 and 44-2 receive the fluid that has passed along branch 118 of channel system 112. In a similar manner, a third pipette 44-3 is disposed such that tip 45-3 receives the fluid exiting along channel 122, and a fourth pipette 44-4 is positioned to receive the fluid from channel 120.

It is to be understood that this particular "quad" embodiment of a collection component is exemplary only. For example, an alternative collection component may include only a first level of branching and thus support only a pair of pipettes. Alternatively, a third level of branches may be included and allow for an even greater number of pipettes (within reason) to be filled during a single procedure.

In the configurations as shown in FIGS. 4-14, the extraction and collection components (needle, tubing and pipette) are disposable. Handle 50 is preferably re-usable, allowing for a significant cost savings while retaining the desired aseptic technique of the procedure.

It is to be understood that many other modifications and other embodiments of the present invention will be apparent to those skilled in the art to which this invention pertains. Therefore, it is to be understood that the invention is not to be limited to the specific embodiments disclosed herein, and any other suitable embodiments are intended to be included within the scope of the appended claims.

What is claimed is:

1. A device for obtaining a small volume fluid sample from an animal, the device comprising
    a handle for one-handed operation by a user; and
    a fluid extraction device disposed at a first end of the handle, the fluid extraction device comprising
    a fluid extraction component disposed at an end termination of the fluid extraction device; and
    a fluid collection component removably attached to the fluid extraction component, the fluid collection component comprising a pipette disposed in fluid communication with the fluid extraction component for receiving the small volume fluid sample through capillary action.

2. The device as defined in claim 1 wherein the fluid extraction component comprises a hypodermic needle removably attached to the fluid collection component.

3. The device as defined in claim 1 wherein the pipette is pre-calibrated to draw a specified volume of fluid.

4. The device as defined in claim 1 wherein the pipette is configured to draw a precise volume of fluid, within a range of +/−10% of a defined volume.

5. The device as defined in claim 1 wherein the pipette includes a bulbous reservoir for holding the collected volume of fluid.

6. The device as defined in claim 1 wherein the device further comprises a quick-release assembly disposed between the fluid extraction component and the fluid collection component, with the fluid extraction component releasably attached to a first end of the quick-release assembly and the pipette releasably attached to a second, opposing end of the quick release assembly.

7. The device as defined in claim 6 wherein the quick-release assembly comprises
    a first end component for engaging with the fluid extraction component;
    a second end component for releasably supporting the pipette; and
    an intermediate component disposed between the first and second end components, the intermediate component providing alignment between the fluid extraction component and the pipette.

8. The device as defined in claim 7 wherein the intermediate component is a sealing disk to minimize leakage of fluid between the hypodermic needle and the pipette.

9. The device as defined in claim 2, wherein the collection component comprises a plurality of pipettes disposed in fluid communication with the hypodermic needle.

10. The device as defined in claim 9 wherein the collection component includes a quick-release assembly including a plurality of channels, each channel associated with a separate one of the plurality of pipettes.

11. The device as defined in claim 1, wherein the extraction component comprises a lancet.

12. The device as defined in claim 11, wherein the lancet is removably attached to the grip handle.

* * * * *